US010806470B2

(12) United States Patent
Lipari et al.

(10) Patent No.: US 10,806,470 B2
(45) Date of Patent: Oct. 20, 2020

(54) PATIENT-SPECIFIC NAVIGATIONAL GUIDE

(71) Applicant: MEDACTA INTERNATIONAL SA, Castel san Pietro (CH)

(72) Inventors: Alberto Lipari, Civate (IT); Meinrad Fiechter, Lugano (CH); Francesco Siccardi, Castel san Pietro (CH)

(73) Assignee: Medacta International SA, Castel San Pietro (CH)

( * ) Notice: Subject to any disclaimer, the term of this patent is extended or adjusted under 35 U.S.C. 154(b) by 180 days.

(21) Appl. No.: 15/526,545

(22) PCT Filed: Nov. 13, 2015

(86) PCT No.: PCT/IB2015/058772
§ 371 (c)(1),
(2) Date: May 12, 2017

(87) PCT Pub. No.: WO2016/075660
PCT Pub. Date: May 19, 2016

(65) Prior Publication Data
US 2017/0311961 A1 Nov. 2, 2017

(30) Foreign Application Priority Data

Nov. 14, 2014 (IT) .............................. MI2014A1969

(51) Int. Cl.
*A61B 17/17* (2006.01)
*A61B 17/56* (2006.01)
(Continued)

(52) U.S. Cl.
CPC .......... *A61B 17/1757* (2013.01); *A61B 17/56* (2013.01); *A61B 17/1796* (2013.01);
(Continued)

(58) Field of Classification Search
CPC ............ A61B 17/1757; A61B 17/1796; A61B 17/1739; A61B 17/17; A61B 17/7076
See application file for complete search history.

(56) References Cited

U.S. PATENT DOCUMENTS 5,928,232 A 7/1999 Howland
2011/0319745 A1* 12/2011 Frey ...................... A61B 17/15
600/407
(Continued)

FOREIGN PATENT DOCUMENTS

EP 2749235 A1 7/2014
TW 201238556 A 10/2012
(Continued)

OTHER PUBLICATIONS

International Search Report and Written Opinion dated Feb. 5, 2016, from International Application No. PCT/IB2015/058772, 12 pages.
International Search Report and Written Opinion dated Jan. 20, 2016 from International Application No. PCT/IB2015/058399, 11 pages.

*Primary Examiner* — Amy R Sipp
(74) *Attorney, Agent, or Firm* — Meunier Carlin & Curfman LLC

(57) ABSTRACT

Patient-specific navigational guide (1) for use in spinal surgery, comprising two tubular guiding members (2) integral with a bearing frame (3) and extending from a proximal opening (2*a*) to a distal opening (2*b*) for guiding a surgical operation on a patient's vertebra (100); contact members (14, 15, 16) designed to match a corresponding plurality of contact areas (103, 102) on the patient's vertebra (100) in order to define a unique coupling configuration of the patient-specific navigational guide (1) on the patient's vertebra (100), wherein said contact members (14, 15, 16) comprise at east one pair of first main contact members (15), designed to abut on a contact area corresponding to the superior articular process (103) or facet of the patient's vertebra (100) and a pair of second main contact members (Continued)

(16), designed to abut at least partially on a contact area corresponding to the laminae (102) of the patient's vertebra (100). Contact members also comprise auxiliary contact members (14), designed to abut at least partially on a contact area corresponding to the edges (102a) of the patient's vertebra (100), in a position different from that of contact of the pair of the second main contact member (16), or to abut at least partially on a contact area corresponding to the transverse process (104).

14 Claims, 4 Drawing Sheets

(51) Int. Cl.
    *A61B 17/88*     (2006.01)
    *A61B 17/84*     (2006.01)
(52) U.S. Cl.
    CPC ......... *A61B 17/848* (2013.01); *A61B 17/8897* (2013.01); *A61B 2017/568* (2013.01)

(56) References Cited

U.S. PATENT DOCUMENTS

| | | | |
|---|---|---|---|
| 2012/0245587 A1* | 9/2012 | Fang | A61B 17/1671 606/80 |
| 2013/0123850 A1* | 5/2013 | Schoenefeld | A61B 17/1757 606/248 |
| 2013/0218163 A1† | 8/2013 | Frey | |
| 2014/0350614 A1* | 11/2014 | Frey | A61B 17/1757 606/86 R |
| 2014/0358152 A1* | 12/2014 | Condino | A61B 17/1757 606/96 |

FOREIGN PATENT DOCUMENTS

| | | |
|---|---|---|
| WO | 2014070889 A1 | 5/2014 |
| WO | 2014090908 A1 | 6/2014 |
| WO | 2014197844 A1 | 12/2014 |

\* cited by examiner
† cited by third party

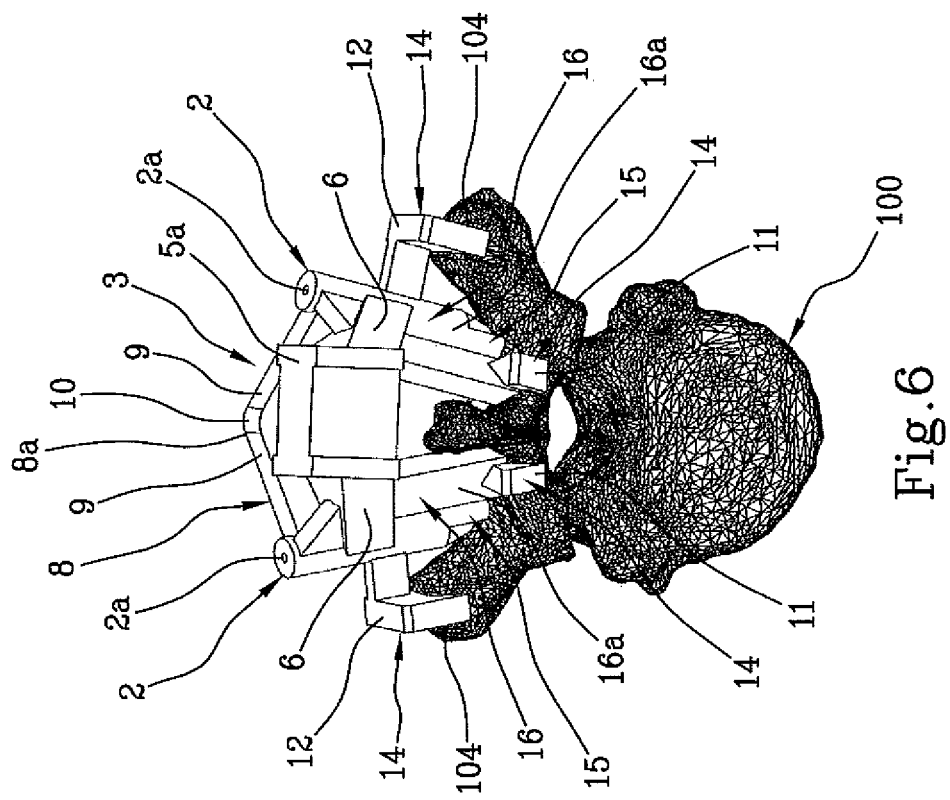
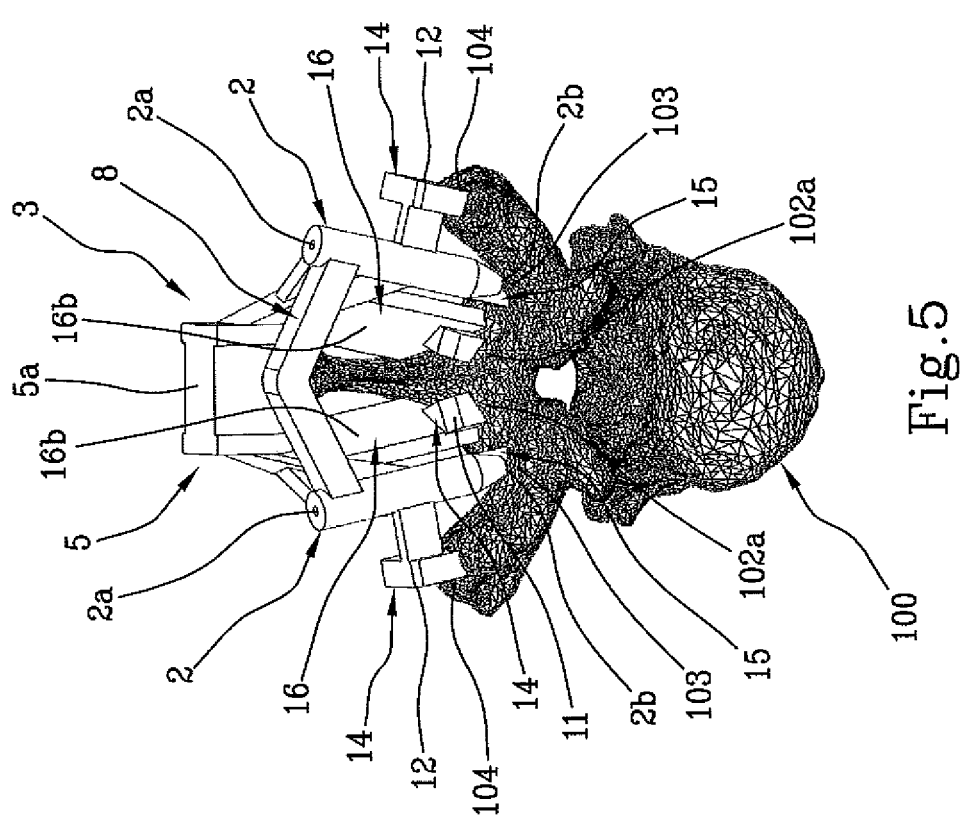

PATIENT-SPECIFIC NAVIGATIONAL GUIDE

TECHNICAL FIELD

The present invention relates to the technical field of orthopaedic surgery. More specifically, the invention relates to a patient-specific navigational guide to be employed in spinal surgery.

Patient-specific guides are disposable templates, which are individually designed to match the bone anatomy derived from CT-scans of a given patient. Surgical operations like drills and cuts can be pre-operatively planned by computer-aided technologies, and the resulting patient-specific guides will later allow the surgeon to accurately replicate the planned operations on the patient's body.

Patient-specific guides have been employed in several fields of orthopaedic surgery, including spinal surgery.

In this field, patient-specific guides are mainly employed to help the surgeon during pedicle screw insertion, so that the screw can be inserted according to a pre-planned optimal axis of the same.

However, patient-specific guides may be used in spinal surgery for other purposes; for instance as cutting guides during PSO (pedicle substraction osteotomies), laminotomy or facectomies.

STATE OF THE ART

Examples of patient-specific guides are known, for example, from patents EP 2749235, EP 2502582, WO 2013/158521, WO 2014/197844, or WO2014/070889.

All these documents show that the guides are generally designed in such a way that they couple with the patient's vertebrae in a stable and well-defined configuration. In order to achieve this goal, it is necessary to have large contact areas between the guide and the bony structure of the patient.

A main contact point which is always used, as it provides great stability to the whole guide, it is the spinous process, in particular the support with its top part.

To properly position the device on the corresponding vertebra, it is necessary to carefully prepare the spinous process area.

Therefore, before the positioning of the guide, the surgeon is forced to clean not only the spinous process, but also a large area of the bone from the surrounding tissue, and in some cases to severe the ligaments.

Specifically, having to free the spinous process area, the surgeon is forced to remove the interspinous and/or supraspinous ligaments This often proves to be a difficult and time-consuming task that it would not be necessary to perform during a "free-hand" surgery, i.e. without the use of the guides in question.

In addition, such a preparatory operation can lead to complications as well as a prolongation of hospitalization of the patient.

Moreover, the remaining tissue that the surgeon is unable to remove may lead to slipping and deviation of the guide, eventually resulting in an incorrect or suboptimal positioning of the pedicle screws or bone resections.

OBJECT OF THE INVENTION

In view of the foregoing, the technical problem underlying the present invention is to provide a patient-specific surgical guide, of the type being used in spinal surgery, which stably and uniquely couples with the patient's vertebra without the need to accurately prepare the spinous process area by severing the ligaments.

Specifically, the technical problem that the present invention aims to solve is to provide a patient-specific surgical guide, of the type used in spinal surgery, allowing fast and easy positioning, which is less invasive for the patient and involving only a few surgical steps for its insertion, thus limiting the margin of error.

The above-mentioned technical problem is solved by a patient-specific navigational guide for use in spinal surgery, according to claim 1.

The invention provides improved stability by means of a plurality of contact points, among which the support on the spinous process is not included.

This spares the surgeon the task of having to clean this area and sever its ligaments. In this way, the insertion of the guide takes place more quickly, easily, with fewer complications and risks, especially those related to cleaning operations of the spinous process.

Despite the absence of contact with the spinous process, the guide is nevertheless highly stable thanks to the presence of at least four contact points which are advantageously present in a variable number from six to eight. This creates a stable structure even in the case where a contact area is damaged during surgery and allows to avoid the use of the spinous process as the main support point.

The guide according to the present invention is suitable for cervical, thoracic, lumbar spine and sacrum.

Further features and advantages of the patient-specific navigational guide according to the invention shall be made clearer by the description, given herein below, of a number of embodiments described by way of non-limiting examples with reference to the accompanying drawings.

BRIEF DESCRIPTION OF THE DRAWINGS

FIGS. 5-7 show perspective views of a third embodiment of the patient-specific navigational guide according to the invention, coupled to a vertebra;

DETAILED DESCRIPTION OF PREFERRED EMBODIMENTS OF THE INVENTION

Figure 1:
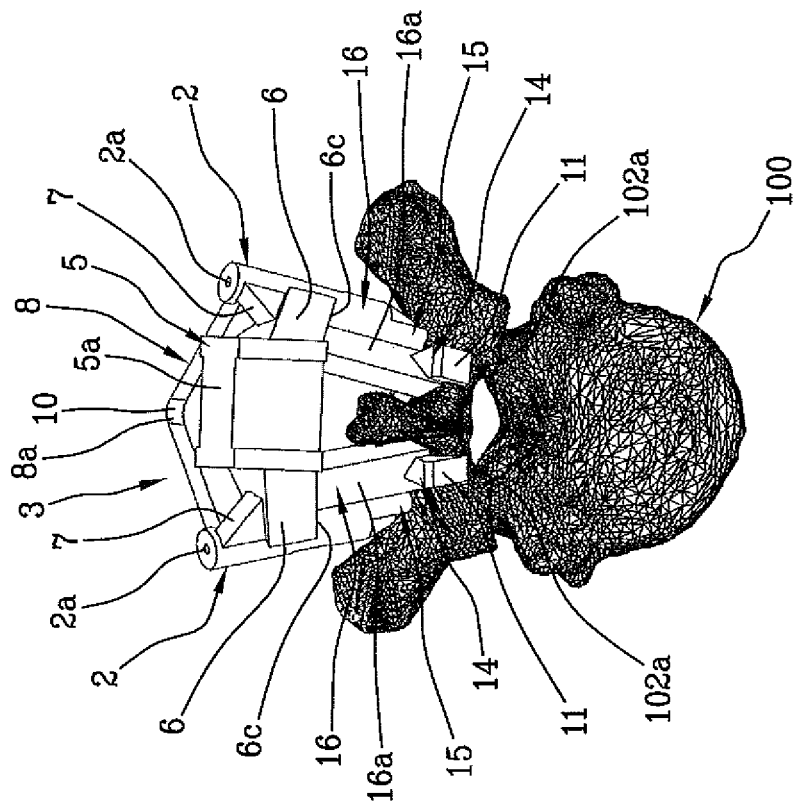
FIGS. 1-2 show perspective views of a first embodiment of the patient-specific navigational guide according to the invention, coupled to a vertebra.
Figure 2:
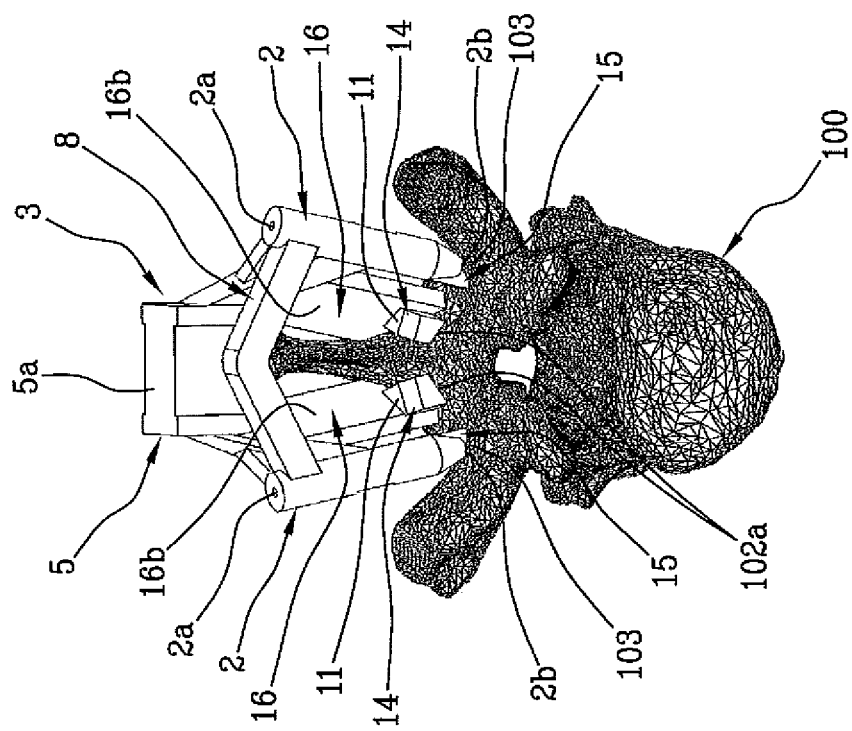

Referring to FIGS. 1-8, an exemplary embodiment of a patient-specific navigational guide 1 for spinal surgery is illustrated, which is specifically designed for operations on a vertebra 100.

As may be readily recognized in these figures, the navigational guide 1 comprises two tubular guiding members 2.

The two tubular guiding members are integral with a bearing frame 3.

The two tubular guiding members 2 define the insertion axes for guide wires or two pedicle screws, which should be inserted in the lumbar vertebra according to a pre-operatively planned angle. The insertion axes correspond to the longitudinal axes of the tubular guiding members 2. Therefore, the tubular guiding members 2 feature a proximal opening 2a, from which a surgical tool could be inserted, and a distal opening 2b in the vicinity of the patient's vertebra. The terms "proximal" and "distal" are used with reference to the surgeon.

The inner diameter of the tubular guiding members 2 is such as to allow the insertion of a Kirchner wire. The Kirchner wire is implanted in the bone and, when the guide 1 is removed, is used to guide a polyaxial screw which runs along the K-wire in order to touch the bone and be implanted. The inner diameter of the tubular guiding members 2 can be large enough to allow passage of a polyaxial screw or of a bone resection instrument, such as a burr. The inner diameter of the tubular guiding members 2 can be selected from 3-18 mm, 3-12 mm, 3-9 mm, 3-6 mm.

The distal opening 2b can comprise a gate forming an open window so that the surgeon can check the entry point of the pedicle screw or Kirchner wire inserted through the tubular guiding members 2.

The bearing frame 3 comprises a V-shaped bridge 5, connecting the two tubular guiding members 2.

The V-shaped bridge 5 has two arms 6: each arm 6 is connected to a tubular guiding member 2 and points toward the caudal direction, so that a vertex 5a of the V-shaped bridge 5 is positioned above the spinous process 101 of the lumbar vertebra 100 without any contact with it.

Each of the two arms 6 has a prismatic shape defined by planar surfaces 6a-6d. The prismatic shape of the arms 6 enlarges from the tubular guiding member 2 to the vertex 5a. In particular each arm 6 comprises a proximal surface 6a and a distal surface 6c, opposed to the proximal surface 6a, each having a substantially triangular shape, and two opposite side planar surfaces 6b, 6d, each having a substantially rectangular shape.

The V-shaped bridge 5, in particular each arm 6, connects the two tubular guiding members 2 at a substantially central portion of each tubular guiding member 2, between the proximal opening 2a and the distal opening 2b.

In particular, the width L of the two opposite planar surfaces 6b and 6d of each arm 6 of the V-shaped bridge 5 defines an extended connecting portion between the tubular guiding members 2 and the V-shaped bridge 5. Preferably, the width L is greater than A/2, in which A is the distance between the proximal opening 2a and the distal opening 2b.

Reinforcing ribs 7 can be provided to connect the arms 6 of the V-shaped bridge 5 to the tubular guiding members 2. In particular, each rib 7 extends from a portion near the proximal opening 2a to the proximal surface 6a of each arm 6.

A non-rectilinear bridge 8 can further connect the two tubular guiding members 2. In particular the non-rectilinear bridge 8 connects proximal portions of the tubular guiding members 2, near the proximal openings 2a, and comprises at least one summit portion 8a defining the more proximal portion of the navigational guide 1.

Considering an inner volume defined by the two tubular guiding elements 2 and the V-shaped bridge 5, the non-rectilinear bridge 8 extends from the proximal portions of the tubular guiding members 2 towards the outside.

Preferably, the non-rectilinear bridge 8 comprises two arms 9, preferably two rectilinear arms 9, connected by a curved portion 10 defining the summit portion 8a.

Preferably, the non-rectilinear bridge 8 remains within a theoretical plane comprising the two tubular guiding members 2. In particular, the non-rectilinear bridge 8 with its summit portion 8a lies on a plane comprising the longitudinal axes of the tubular guiding members 2. This arrangement allows to improve stability of the guide 1.

The known guides have the risk of deformation which causes a deviation between the planned and actual screw position. The screw can be wrong positioned and can severely damage the neural structure for these kind of applications. The non-rectilinear bridge makes the guide stable regarding medial lateral deformation at the position of the wire/screw entry point.

Indeed, the arrangement of the non-rectilinear bridge 8 prevents any deflection of the guide (that is, that the two tubular guiding members 2 cannot approach one another) and guarantees the accuracy for K-wire/screw placement. Therefore the guide 1 allows to avoid errors (due to elastic deformation of the bridge 8) when the K-wire/screw is positioned.

The non-rectilinear bridge 8 and the V-shaped bridge 5 can be arranged to form an angle of at least 90° between the theoretical plate comprising the non-rectilinear bridge 8 and two tubular guiding members 2 and the theoretical plate comprising the V-shaped bridge 5.

Figure 8:
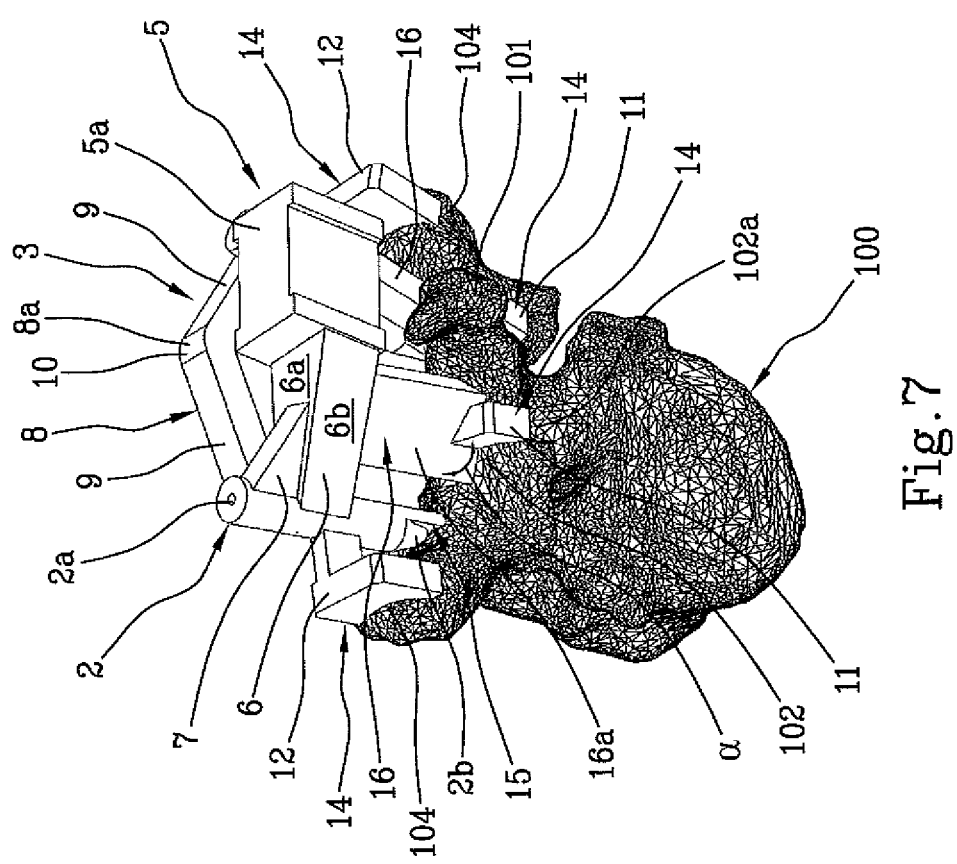
FIG. 8 shows a perspective view of an alternative embodiment of the patient-specific navigational guide according to the invention, coupled to a vertebra.

An alternative configuration, shown in FIG. 8, presents a patient-specific navigational guide lacking such non-rectilinear bridge 8. Stability, in this case, is guaranteed by the high number of contact points in the guide, as will be explained hereinbelow.

The pre-operatively planning is performed, by means of computer-aided design tools, on a three-dimensional model of the bony structure developed from a three-dimensional image (e.g. CT/MRI scan) of the patient. Therefore, the navigational guide 1 is designed in such a way that it uniquely matches the bony structure of the patient.

In particular, to ensure a correct and stable positioning of the navigational guide 1, a plurality of contact members are provided, each of them being designed to match a corresponding contact area on the patient's vertebra 100.

Advantageously, the main contact areas correspond to the edges 102 and the superior articular process 103 or facet.

The plurality of contact members comprises a pair of main contact members 15 intended to couple with a main contact area, corresponding to the superior articular process 103 or facet of the vertebra 100.

In the present embodiment, each of the first main contact members 15 comprises a contact finger, projecting from the a respective tubular guiding member 2, near the distal opening 2b, downwards in respect to the V-shaped bridge 5. The free end of said contact fingers is designed with a shape matching the superior articular process 103 or facet of the patient's vertebra 100. It is noted that the contact finger extends from a caudal/inner portion of the tubular guiding member 2 and is directed toward the median plane and away from the vertex of the V-shaped bridge 5.

In a further embodiment, not illustrated, the contact finger is not present and the distal opening 2b is shaped so as to match the anatomical shape of the superior articular process or facet, thus defining the main contact member. Moreover, the plurality of contact members comprises a pair of a main contact member 16 intended to abut on a main contact area corresponding, at least partially, to the lamina 102 of the patient's vertebra 100.

Figure 3:
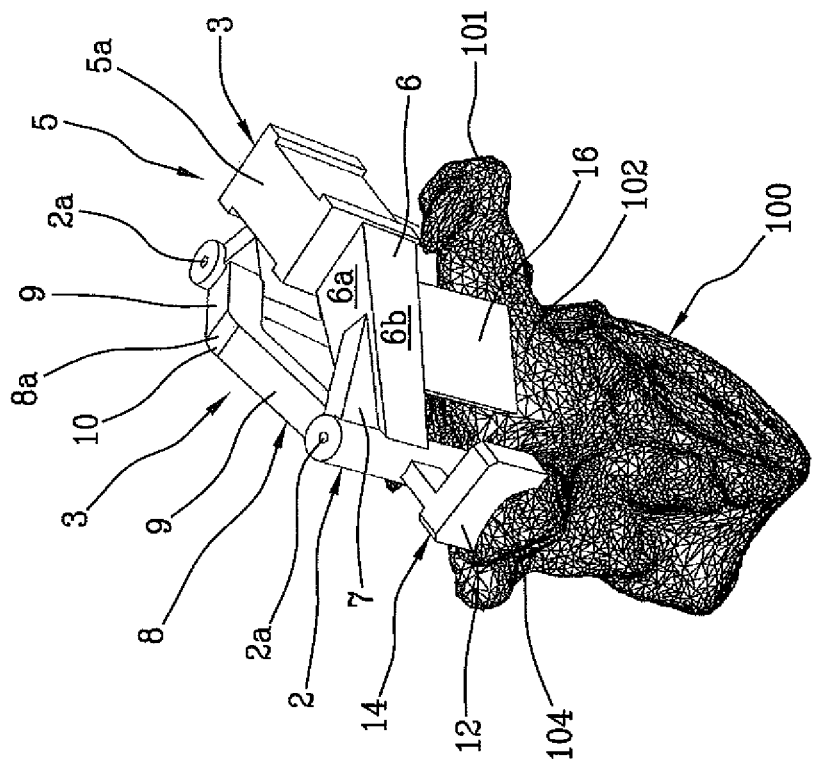
FIGS. 3-4 show perspective views of a second embodiment of the patient-specific navigational guide according to the invention, coupled to a vertebra.
Figure 4:
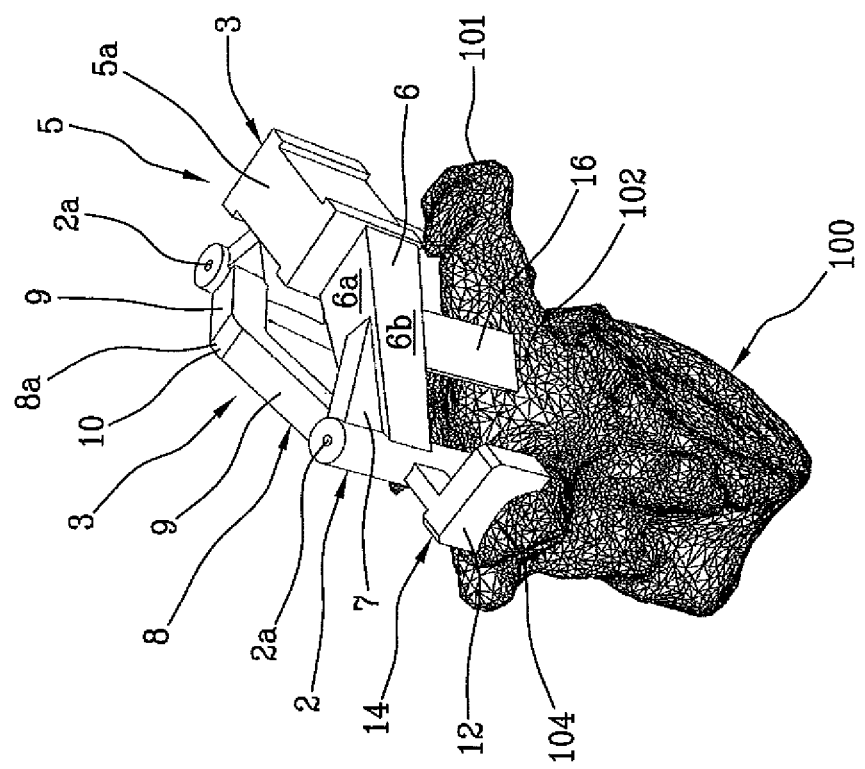
Figure 7:
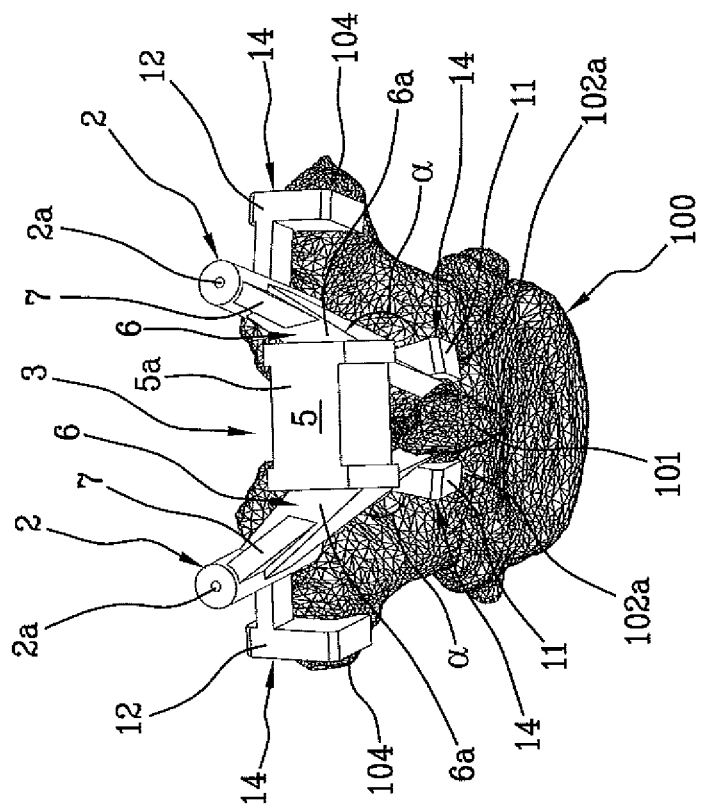

Each second main contact member 16 extends from a respective arm 6 defining the V-shaped bridge 5, abutting, at least partially, on the lamina 102 of the vertebra 100. Preferably, each second main contact member 15 is a lamella and thus presents a planar, preferably polygonal shape, which develops in a direction substantially parallel to the longitudinal axes of the tubular guiding members 2. Preferably, these lamellae have a transverse extension between 5 and 60 mm, preferably between 5 and 40 mm. In FIGS. 3 and 4, for example, two different dimensions of the lamella 16 are illustrated.

If the size of the lamella, thus of the second main contact member 16, is generous, it is possible to obtain a partial contact with a side portion of the spinous process.

The two first main contact members 15, as well as the two second main contact members 16, are symmetrically positioned on the navigational guide 1, with respect to a median plane passing through the top vertex 5a of the V-shaped bridge 5. However, depending on the patent anatomy, an asymmetrical arrangement is also possible.

Always with respect to a median plane passing through the top vertex 5a of the V-shaped bridge 5, the two first main contact members 15 are placed laterally and externally compared to the two second main contact members 16; in other words, the second main contact members 16 are positioned between the vertex 5a of the V-shaped bridge 5 and the first main contact members 15.

Also provided are auxiliary contact members 14, likewise designed to abut at least partially on a contact area corresponding to the edges 102a of the patient's vertebra 100, in a position different from that of contact of the pair of the second main contact member 15, or to abut at least partially on a contact area corresponding to the transverse process 104.

In other words, in a first embodiment (FIGS. 1, 2), the auxiliary contact members 14 may include a pair of auxiliary contact members 11 designed to abut at least partially on a contact area corresponding to the laminae 102a, in a position adjacent to the contact area corresponding to the laminae 102 on which the second main contact members 16 rest.

Such pair of auxiliary contact members 11 comprises at least one appendix extending from each of the second main contact members 16. Said appendix 11 is preferably disposed transversely with respect to the respective second main contact member 16, in such a way as to define, with a planar surface 16a of the latter, an angular sector α, running around a corner portion of the lamina 102. Advantageously, the appendix 11 can be present on both planar surfaces 16a and 16b of the lamella of the second main contact members 16.

Appendix 11 allows to increase the stability in the sagittal direction.

This allows a combined and strengthened support since the resulting contact surface is greater: in addition to the support given by the lamella 16 of the second main contact members, which rests on the lamina 102, there is also the contact of the appendix 11 that runs around the angle of the lamina 102 to better envelop a portion of the vertebra 100, almost "clinging" to it.

Preferably, the appendix 11 has minimum dimensions in width (i.e. along the direction extending from tubular guide to tubular guide) and height (the direction extending from the proximal opening to the distal opening) of at least 3 mm; preferably it protrudes from the lamella for at least 1 mm.

In a second embodiment (FIGS. 3, 4), the auxiliary contact members 14 may include a pair of auxiliary contact members 12, designed to abut on a contact area corresponding to the transverse process 104. Alternatively, this same pair of auxiliary contact members 12 can abut partially on a contact area corresponding to the transverse process 104 and partially on a contact area corresponding to the facet 103 or superior articular process of the vertebra 100.

Each auxiliary contact member 12, according to this second configuration, is connected to a respective tubular guiding member 2 at a substantially central portion of the latter, between the proximal opening 2a and the distal opening 2b.

With respect to a median plane passing through the top vertex 5a of the of the V-shaped bridge 5, each auxiliary contact member 12, according to this second configuration, extends from the corresponding tubular guiding member 2, laterally and outwardly.

Preferably, the auxiliary contact members 12 according to this second configuration are substantially T-shaped. The stem of the T is connected to tubular guiding member 2 while the head of the T, transverse to the stem, leans on the corresponding contact area. The auxiliary contact members 12 according to this second embodiment may have an asymmetrical shape: in other words, the head of the T is not necessarily positioned symmetrically with respect to the stem.

Preferably, each auxiliary contact member 12 has minimum dimensions, in each of three directions, of 3 mm.

A third configuration, shown in FIGS. 5-8, presents both embodiments of the auxiliary contact members 14: therefore, there is a first pair of auxiliary contact members 11, designed to abut on a contact area corresponding to the laminae 102a of the vertebra 100, and a second pair of auxiliary contact members 12, designed to abut on a contact area corresponding to the transverse process 104 or partially on a contact area corresponding to the transverse process 104 and partially against the facet 103 or superior articular process of the vertebra 100.

The surgical procedure employing a patient-specific navigational guide 1 comprises a pre-operative planning and an intra-operative procedure.

The pre-operative planning comprises a first step of acquiring CT/MRI scans of the surgical site, a second step of reconstructing a three-dimensional image of the site and a third step of planning the placements of a generic surgical instrument (screws, K-wire or burr) on the three-dimensional image by means of computer-aided design tools.

Once the screw axes or the cutting planes have been identified, the steps of designing and producing the patient-specific navigational guide 1 are performed.

The intra-operative procedure is described below with reference to the patient-specific guide 1.

The procedure includes a step of cleaning the vertebra without cutting the ligament, since the guide should not be in contact with the upper part of the spinous process. The interspinous and/or supraspinous ligaments are preserved, so as to allow an easier and faster insertion of the guide. The surgery is thus less invasive for the patient and the surgeon will have fewer steps to perform (less soft tissue to be removed) with consequent reduction of the margin of error. The stability of the guide is ensured by six or eight contact points.

Subsequently, a step of coupling the guide to the clean vertebra is provided. It is to be noted that, prior to the coupling, the correct location and alignment of the guiding members 2 can be checked on a real size three-dimensional model of the vertebra.

After the coupling, two awls are inserted into the tubular guiding members 2. After removal of the awls the surgeon can check the entry points for the pedicle screws. In the next step, the pedicle of the vertebra is opened with a probe or drill inserted in the guiding member 2. The surgeon can use a feeler to help himself in the process. Finally, after removing the probes or drills, the pedicle screws can be inserted via the tubular guiding members 2 by means of a screwdriver.

In an alternative method, the adapter sleeve is capped on top of the tubular guiding members 2 and two Kirchner wires are inserted into the vertebra instead of directly fixing the pedicle screws. After removal of the navigational guide, the Kirchner wires are used to guide the insertion of a cannulated pedicle screw.

Obviously a person skilled in the art, in order to meet specific needs, will readily acknowledge the possibility of changes and variations to the navigational guides described above, comprised within the scope of protection as defined by the following claims.

The invention claimed is:

1. A patient-specific navigational guide for use in spinal surgery, the guide comprising two tubular guiding members integral with a bearing frame and extending from a proximal opening to a distal opening for guiding a surgical operation on a patient's vertebra; contact members designed to match a corresponding plurality of contact areas on the patient's vertebra in order to define a unique coupling configuration of the patient-specific navigational guide on the patient's vertebra, wherein said contact members comprise at least one pair of first main contact members designed to abut on a contact area of the plurality of contact areas corresponding to a superior articular process or facet of the patient's vertebra and a pair of second main contact members designed to abut at least partially on a contact area of the plurality of contact areas corresponding to a laminae of the patient's vertebra, the guide further comprising auxiliary contact members designed to abut at least partially on a contact area of the plurality of contact areas corresponding to the laminae of the patient's vertebra in a different position from that of the pair of the second main contact members or to abut at least partially on a contact area of the plurality of contact areas corresponding to a transverse process; wherein the bearing frame comprises a V-shaped bridge connecting the two tubular guiding members and comprising two arms, each arm being connected to a tubular guiding member of the two tubular guiding members and pointing toward a caudal direction, so that a vertex of the V-shaped bridge is positioned above a spinous process of the patient's vertebra and without any contact with the spinous process.

2. The patient-specific navigational guide according to claim 1, wherein a respective second main contact member extends from each arm defining the V-shaped bridge and abuts against the lamina of the vertebra.

3. The patient-specific navigational guide according to claim 1, wherein each of the first main contact members comprises a contact finger protruding from the tubular guiding member near the distal opening along a longitudinal direction of the tubular guiding member.

4. The patient-specific navigational guide according claim 1, wherein said auxiliary contact members comprise a first pair of auxiliary contact members designed to abut on a contact area corresponding to the laminae of the patient's vertebra or a second pair of auxiliary contact members designed to abut on a contact area of the plurality of contact areas corresponding to the transverse process.

5. The patient-specific navigational guide according to claim 4, wherein each of said first pair of auxiliary contact members comprises an appendix of each of the second main contact members arranged transversely with respect to said second main contact members, in such a way as to define with a planar surface of the respective second contact member from which the appendix protrudes, an angular sector (a) running around a corner portion of said lamina.

6. The patient-specific navigational guide according to claim 4, wherein each of said second pair of auxiliary contact members abuts partially on a contact area of the plurality of contact areas corresponding to the transverse process and partially on a contact area of the plurality of contact areas corresponding to the superior articular process or facet of the vertebra.

7. The patient-specific navigational guide according to claim 1, wherein each of a second pair of auxiliary contact members connects to a respective tubular guiding member of the two tubular guiding members at a substantially central portion of the respective tubular contact member between the proximal opening and the distal opening.

8. The patient-specific navigational guide according to claim 7, wherein each of the second pair of auxiliary contact members is substantially T-shaped and extends laterally outwardly from the respective tubular guiding member of the two tubular guiding members with respect to a vertical median plane of the guide.

9. The patient-specific navigational guide according to claim 1, wherein said second main contact members are lamellae having a transverse extension between 5 and 60 mm.

10. The patient-specific navigational guide according to claim 9, wherein said second main contact members also abut partially on a side portion of the spinous process.

11. The patient-specific navigational guide according to claim 1, wherein the V-shaped bridge connects the two tubular guiding members at a substantially central portion of each tubular guiding member of the two tubular guiding members between the proximal opening and the distal opening.

12. The patient-specific navigational guide according to claim 1, wherein the bearing frame also comprises a non-rectilinear bridge further connecting directly the two tubular guiding members at proximal portions of the tubular guiding members near the proximal openings and comprises at least one summit portion defining a more proximal portion of the navigational guide.

13. The patient-specific navigational guide according to claim 12, wherein considering an inner volume defined by the two tubular guiding members and the V-shaped bridge, the non-rectilinear bridge extends from proximal portions of the tubular guiding members towards an outside.

14. The patient-specific navigational guide according to claim 13, wherein the non-linear bridge comprises two straight arms connected by a curved portion defining a top portion; said non-linear bridge lying with the top portion in a plane comprising a longitudinal axes of the tubular guiding members.

* * * * *